US006858434B1

(12) United States Patent
Williams

(10) Patent No.: US 6,858,434 B1
(45) Date of Patent: Feb. 22, 2005

(54) METHOD FOR SYNTHESIS, SEPARATION AND SCREENING OF A PLURALITY OF COMPOUNDS IN THE SAME BULK OF A STATIONARY PHASE

(75) Inventor: Lorenzo Williams, Oslo (NO)

(73) Assignee: Sinvent AS, Trondheim (NO)

( * ) Notice: Subject to any disclaimer, the term of this patent is extended or adjusted under 35 U.S.C. 154(b) by 0 days.

(21) Appl. No.: 09/680,471

(22) Filed: Oct. 6, 2000

(30) Foreign Application Priority Data

Oct. 6, 1999 (NO) ................................................ 994873

(51) Int. Cl.[7] .............................................. G01N 30/02
(52) U.S. Cl. ........................... 436/161; 436/162; 436/2
(58) Field of Search ................................. 436/161, 162, 436/2, 34, 44, 71, 95, 150, 169, 172, 37; 422/56, 68.1, 69, 70, 66, 67, 82.08, 82, 82.09; 435/4, 29; 356/317

(56) References Cited

U.S. PATENT DOCUMENTS

| | | | | | |
|---|---|---|---|---|---|
| 4,059,405 | A | * | 11/1977 | Sodickson et al. | 436/44 |
| 4,666,863 | A | * | 5/1987 | Edwards et al. | 436/514 |
| 4,717,656 | A | * | 1/1988 | Swanljung | 435/7.92 |
| 4,956,302 | A | * | 9/1990 | Gordon et al. | 436/161 |
| 6,965,193 | | * | 10/1990 | Chen | 435/18 |
| 5,332,665 | A | * | 7/1994 | Reed | 435/70.21 |
| 5,482,372 | A | * | 1/1996 | Bataillard et al. | 374/31 |
| 5,739,003 | A | * | 4/1998 | Brocklehurst et al. | 435/29 |
| 5,847,105 | A | * | 12/1998 | Baldschwieler et al. | 536/25.3 |
| 6,034,361 | A | * | 3/2000 | Hudak | 219/702 |
| 6,306,590 | B1 | * | 10/2001 | Mehta et al. | 435/6 |

FOREIGN PATENT DOCUMENTS

| DE | 3701833 A1 | * | 8/1987 | ........... C12Q/1/00 |
|---|---|---|---|---|
| JP | 03099264 | * | 9/1989 | |
| WO | A1 WO 9408051 | | 4/1994 | |

OTHER PUBLICATIONS

Soljic et al., "Possibility of formation of colored spots of inorganic ions with organic reagents on thin layers of cellulose and silica gel. II" : Kemija u Industriji (1997), 46(5), 195–202 (Abstract).*

Margotat et al. "A rapid and simple assay for the study of thromboxane B2 synthesis by intact human platelets", J. Pharmacol. Methods (1983), 9(1), 63–70.* http://www.harcourt.com/dictionary/def/9/0/7/3/9073700.html, Academic Press Dictionary of Sciences and Technology.*

Margotat et al. "A rapid and simple assay for the study of thromboxane B2 synthesis by intact human platelets", J. Pharmacol. Methods (1983), 9(1), 63–70 (Abstract).*

J.J. Espinosa–Aguirre, et al., "Bacterial mutagens in the urine of patients under tinidazole treatment"; Mutation Research 359 (1996) pp. 133–140.

Michael Feemantle, "TLC Used As Tool For Combinatorial Synthesis", Mar. 13, 2000.

Lorenzo Williams, "Thin layer chromatography as a tool for reaction optimisation in microwave assisted synthesis", The Royal Society of Chemistry (2000), pp. 435–436.

(List continued on next page.)

Primary Examiner—Yelena G. Gakh
(74) Attorney, Agent, or Firm—Birch, Stewart, Kolasch & Birch, LLP

(57) ABSTRACT

A method for sequentially performing a synthesis, separation and screening of chemical entities, especially a combinatorial library, is described. The method utilises a bulk of a stationary phase (e.g. silica gel, aluminium oxide, cellulose, etc. for example arranged on a backing) for the performance of the synthesis, separation and screening. The technique described enables a rapid route from synthesis to the testing of chemical compounds. Screening can be performed without need for reaction work-up. Preferred screening methods are those used to determine the biological activity of the compounds.

36 Claims, 19 Drawing Sheets

OTHER PUBLICATIONS

A. Bjorseth, et al. "Detection of Mutagens in Complex Samples by the Salmonella Assay applied Directly on Thin–Layer Chromatography Plates" Science. vol. 215 (Jan. 1, 1982) pp. 87–89.

Chung–Ming Sun, "Recent Advances in Liquid–Phase Combinatorial Chemistry" Combinatorial Chemistry & High Throughput Screening, 1999, vol. 2 pp. 299–318.

Houghton, P.J., et al. "Antimicrobial activity of extracts of some Bignoniaceae from Malaysia" Pharmaceutical and Pharmacological Letters 7 (1997)2/3: pp. 96–98.

Ronald Frank, "Spot–Synthesis: An Easy Technique for the Positionally Addressable, Parallel Chemical Synthesis on a Membrane Support", Tetrahedron vol. 48, No. 42, (1992) pp. 9217–9232.

Charles P. Woodbury Jr., et al. "Methods of screening combinatorial libraries using immobilized or restrained receptors" Journal of Chromatography B. 725 (1999) pp. 113–137.

Lorenzo Williams, "A Combinatorial Approach to the Synthesis of a Piperazine Library", Feb. 4, 1999.

Lorenzo Williams, et al. "A Combined Technology for the Synthesis, Separation, Screening and Analysis of a Combinatorial Library" Feb. 9, 2000.

Lorenzo Williams, et al. "A Combined Technology for the Synthesis, Separation, Screening and Analysis of a Combinatorial Library" Mar. 6, 2000.

K. K. Das et al., Analytical Biochemistry, 143, pp. 125–134 (1984).

K. Laufer et al., Journal of Chromatography A., 684, pp. 370–373 (1994).

K. C. Nicolaou et al., Angewandte Chemie, 34(20) (Nov. 3, 1995), XP000535261.

Jose Barluenga et al., Tetrahedron, 53(27), pp. 9323–9340 (1997).

A.H.M.T. Scholten et al., Journal of Liquid Chromatography, 2(4), pp. 607–617 (1979).

* cited by examiner

A) Synthesis occurs on the X-axis

B) Separation occurs on the Y-axis

C) Screening occurs via transferral or diffusion through the Z-axis, into or on another plane

A

B

A

B

A

B

A

B

A

B

C

A

B

C

METHOD FOR SYNTHESIS, SEPARATION AND SCREENING OF A PLURALITY OF COMPOUNDS IN THE SAME BULK OF A STATIONARY PHASE

FIELD OF THE INVENTION

The present invention relates to the field of preparation and screening of an organic compound, in particular a plurality of organic compounds. Thus, the invention is particularly relevant in the field of rapid preparation and screening of lead structures for drug candidates. The invention provides a method for preparing and screening one or more compound in which method one or more compounds are sequentially prepared, separated and subsequently screened, optionally the compounds are analysed. One interesting characteristic of the present invention is that the synthesis, separation and screening are conducted in one and the same bulk of a material. This offers interesting advantages in that tedious isolation and purification can be avoided while at the same time the prepared compounds are sufficiently isolated for screening to be conducted.

BACKGROUND OF THE INVENTION

Presently there are no known methods that combine the three key areas of synthesis, separation and screening. Other technologies which have partial accomplishments in these areas are based on solid phase parallel/combinatorial synthesis whereby synthesis, purification by washing and sometimes, but rarely, biological evaluation are performed (see for example "Combinatorial Chemistry: Synthesis and Application" eds. S. R. Wilson and A. W. Czarnik, John Wiley & Sons Inc., NY, 1997). These methods require attachment and sometimes cleavage reactions to and from a support. Furthermore, the reactions involved are restricted to those applicable for solid phase chemistry. The normal scope of synthetic chemistry maybe somewhat restricted here, since most reactions are developed in solution. Reactions are often driven to completion by the use of a vast excess of one of the reagents. Purification is usually achieved by sequentially washing the resin or solid support. Biological testing has been performed on compounds still attached to solid supports, though it is unknown as to how this effects the results of these assays, see e.g. WO 94/08051. Spot-synthesis involves the synthesis of compounds on a paper support (R. Frank, Tetrahedron (1992) 48, 9217–9232). Biological screening can then be performed upon the support. However, the purification of compounds is entirely reliant upon sufficient washing of the support. Furthermore, the technique is rather unidimensional in that reactions must be high yielding if not quantitative since the method lacks a separation step.

Solution chemistry has been used to try and overcome some of the disadvantages above. However, in order to screen compounds synthesised in solution, the compounds often need to be isolated. Furthermore, methods for purification can often be complex, requiring the use of sequestering reagents, extractions, column chromatography, etc. In both solution and in the solid phase it is critical that the chemistry is optimised. Chemistry validation is regarded as the bottle-neck in library synthesis and can be a substantial drain on resources. Today's technology is often very complex, time consuming and difficult to integrate. Expensive equipment is usually necessary to achieve the end-goal of screening new compounds.

Bioautography encompasses both the separation of compounds from a mixture and their subsequent biological testing, e.g. P. J. Houghton et al, Pharm. Pharmacol. Lett (1997), 7, 96–98. This technique, to our knowledge, has not been combined with synthesis. It has largely been used in the identification and isolation of natural products. The compounds are then screened in situ.

U.S. Pat. No. 6,029,498 describes a method for performing a chromatographic process under the influence of microwaves and a chromatographic column adapted therefor.

Bjørseth et al., Science, Vol 215, 1 January 1982, pp 87–89, describe a technique in which components in complex samples are separated on thin-layer chromatography plates and their mutagenic effect is registered directly on the plates by means of a *Salmonella* assay. Espinosa-Aguirre et al, Mutation Research 359 (1996) 133–140, describe the detection of bacterial mutagens by utilising the technique described by Bjørseth et al.

Thus it can be seen from the above discussion that it would be an improvement to the art to provide an integrated system for both combinatorial synthesis and bioassay or other such screening procedure.

SUMMARY OF THE INVENTION

The present invention provides a novel method for the synthesis and screening of one or more compounds in the same bulk of a stationary phase, the method comprises the sequential steps of (a) synthesis of the compound(s) by a chemical reaction performed directly in the bulk of the stationary phase, (b) separation of the compound(s) in the same bulk of stationary phase and (c) direct screening of the separated compound(s) in or on the bulk of stationary phase. Alternatively, the separated compound(s) may be analysed either directly when present in or on the stationary phase, or as an isolated sample(s).

DESCRIPTION OF THE INVENTION

Figure 1:
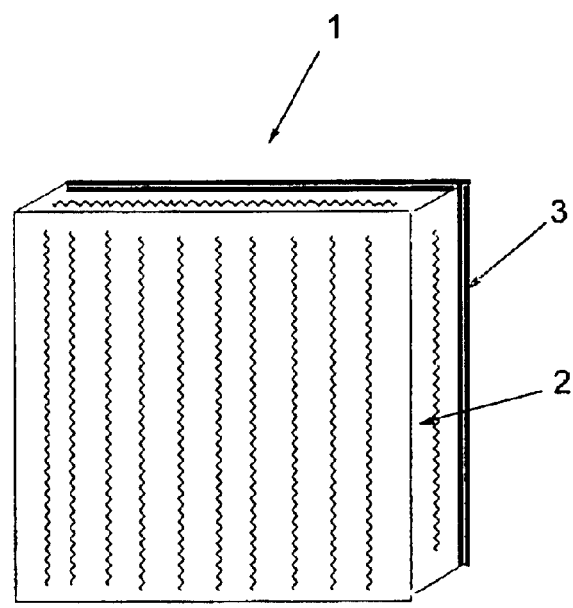
FIG. 1 illustrates an example of a suitable bulk of a stationary phase to be utlilsed in the method of the invention, namely a thin-layer chromatography (TLC) plate, 1, having a stationary phase, 2, typically silica gel, supported by an aluminium backing, 3.
Figure 2:
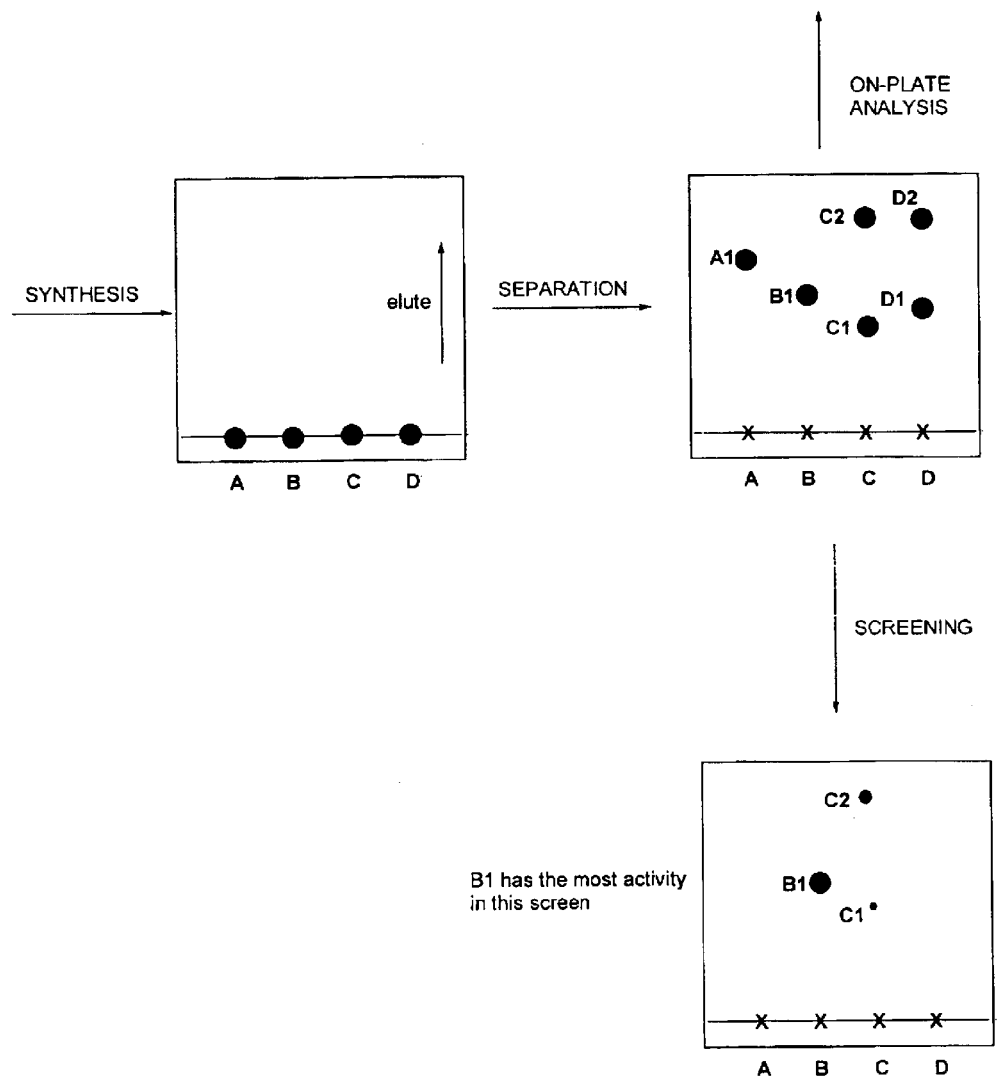
FIG. 2 illustrates how a TLC plate can be utilised within the present invention. The synthesis is performed by providing one or more reaction reagents on localised areas (A–D) of the TLC plate. The separation is performed by eluting the TLC plate with a suitable liquid phase so as to separate the reaction mixture which may comprise one or more compounds (such as reaction product, side products, unused reagents, etc.). The separation is usually conducted so that the compound(s) are allowed to migrate in the bulk of the stationary phase. The separated reaction mixtures are represented with the spots A1, B2, C1, C2, D1, D2. The screening is conducted by one of many possible techniques, e.g. overlay techniques, as will be discussed further below. In addition hereto, the separated compounds may be analysed either by non-destructive means or destructive means. In some instances, analysis is performed on a small aliquot of the spot bearing the compound of interest. In the illustration, spots B1, C1 and C2 exhibit a biological activity, B1 being the most active.

In an attempts to develop a less time consuming and more cost efficient method for the synthesis and screening of one or more chemical compounds, in particular libraries of chemical compounds, a novel method comprising synthesis, separation and screening in the same bulk of a stationary phase has been developed.

The novel method comprises the sequential steps of (a) synthesis of the compound(s) by a chemical reaction performed directly In the bulk of a stationary phase, (b) separation of the compound(s) in the same bulk of stationary phase and (c) direct screening of the separated compound(s) in or on the bulk of the stationary phase. Additionally, the separated compound(s) may be analysed either in or on the stationary phase or as an isolated sample(s). The analysis may take place either before or after the separation step, most often after.

The term "stationary phase" is intended to mean a coherent or non-coherent material which can have adsorbent and non-adsorbent properties. The stationary phase may consist of particles, fibres, a gel, etc. In a preferred embodiment of the invention, the stationary phase utilised is somehow porous so as to allow some mobility of the compounds present therein in the separation step and possibly also in the screening step. The stationary phase is preferably selected from silica gel, aluminium oxide, cellulose, ion exchange materials, graphite, molecular sieves and polymers such as polyacrylamide gel. More specific examples of adsorbent materials are Florosil, Sephadex and Kieselguhr. Other suitable examples of adsorbent materials are described in "Thin-Layer Chromatography" by B. Fried and J. Sherma (4$^{th}$ ed., Chromatographic Science Series Volume 81, Marcel Dekker, Inc., New York, 1999, Viii+499 pp.). The stationary phases may in addition comprise a polymeric binder or a gypsum/polymer binder as well as an indicator.

The term "bulk of a stationary phase" is intended to mean a rather well defined portion of a stationary phase which is arranged in a desired shape, i.e. like a three-dimensional object. In order to fully exploit the bulk of a stationary phase, it is advantageous that the bulk is arranged in a sheet-like format, thereby allowing for an optimal geometrical separation of compounds in different areas of the bulk (optimal resolution in the separation step). The material can, e.g., be arranged in the form of a matrix, a sheet, a cloth or as a membrane (particularly relevant for polymeric materials). Furthermore, the stationary phase may consist of two or more different materials having quite similar or even quite different properties. The stationary phase may also include other constituents so as to moderate the performance of the synthesis, separation or screening step (or any analysis step, e.g. when using a UV indicator when the analysis involves UV detection)

In one embodiment of the invention, the bulk of the stationary phase comprises different materials, mixtures of materials or combinations thereof, arranged in well-defined adjoining areas ether in a vertical manner such as in a sandwich structure or in a horizontal manner. In these cases, it is envisaged that the separation step may bring the compounds from one stationary phase material to another stationary phase material. It is however currently believed that that bulk of the stationary phase should be relatively homogeneous at the macroscopic level so as to eliminate interface effects in the separation step.

As the bulk of the stationary phase preferably is in a sheet-like form, it may be necessary or desirable to support the bulk, in particular where the stationary phase consists of non-coherent particles or fibres or of a flexible or brittle gel. In a preferred embodiment of the invention the bulk of stationary phase is dispersed onto or between an inert backing such as sheets or plates of glass, plastic, fibrous materials, paper, metals or mixtures thereof such as aluminium coated paper.

The size and shape of the backing is important only in terms of resolution. A 10 cm×10 cm size plate or sheet of backing is often adequate for most purposes. However, larger plates or sheets of backing, e.g. 20 cm×20 cm, allow for at least 40 different parallel syntheses, separations and screenings. The backing may have different shapes such as squared, rectangular or circular, in which case different techniques for the separation of the synthesised compound(s) must be applied, e.g. circular backings require radial chromatography techniques.

When dispersed on to or between an inert backing the layer thickness of the bulk of stationary phase is normally 10 $\mu$m to 5 mm, preferably 10 $\mu$m to 2 mm, more preferably 100 $\mu$m to 250 $\mu$m. A thickness of more than 5 mm will normally result in an undesired migration of the compounds in the direction of the thickness during both the synthesis and the separation steps and at the same time an insufficient migration of the compounds in the screening step.

In one embodiment of the invention the combined bulk of stationary phase and backing constitutes a silica gel thin-layer chromatography plate with a glass backing. In another embodiment of the invention the combined bulk of stationary phase and backing constitute a silica gel thin-layer chromatography plate with an aluminium backing. In yet another embodiment of the invention the combined bulk of stationary phase and backing constitute a silica gel thin-layer chromatography plate with plastic backing. For these three embodiments, the separation step typically involves liquid phase chromatography.

In a further embodiment of the invention the bulk of stationary phase comprises a polyacrylamide gel enclosed between to two glass or plastic backing plates. For this embodiment, the separation step typically involves electrophoresis.

Another arrangement of the bulk of a stationary phase is as a self-supporting gel which can be formed e.g. as a sheet or as a cylinder. Such as gel may be cut into slices before screening (see below).

Characteristic for the method is that the compound(s) is synthesised directly in the bulk of the stationary phase. The reaction mixture is obtained by introducing the necessary chemical reagents to a well-defined area on the bulk of stationary phase. The chemical reagent may be introduced on the bulk of stationary phase either as the concentrated chemical itself or in a suitable concentration in a solution either by itself or together with other chemical reagents such as a catalyst for the reaction. The solution may comprises one or more different solvents compatible with the chemical reagent such as methanol, ethanol, ethyl acetate, dichloromethane, ethyl ether, acetonitrile, tetrahydrofuran, benzene, toluene, pyridine, N,N-dimethylformamide, methyl sulfoxide and water. Case should also be taken that the solvent or reagents do not have detrimental effect on the stationary phase or the backing (if relevant).

In the present invention the term "chemical reagents" Is intended to cover organic and inorganic chemicals including catalysts as well as substrates and enzymes. It is important to note that the combination of chemical reagents on the bulk of a stationary phase provides the necessary components for performing the desired reaction(s) or reaction type(s). This being said, it should be noted that the material of the stationary phase may be somewhat involved in the chemical reaction (see below).

The present invention can involve a vast number of chemical reactions, e.g. selected from but not restricted to oxidation reactions, reduction reactions, substitution reactions, derivatisation reactions, elimination reactions, reactions giving rise to the formation of covalent bonds and enzymatic reactions.

In one particularly interesting embodiment of the invention the chemical reaction(s) is assisted by exposing the bulk of stationary phase comprising the reaction mixture(s) to microwave radiation, e.g. placing the stationary phase in a microwave cavity such as a microwave oven or an automated microwave apparatus.

The reaction rate of the chemical reactions may furthermore be increased by performing the reaction in the presence of a polar solvent, e.g. N,N-dimethylformamide and methyl sulfoxide both increase the reaction rate of microwave assisted reactions, due to an increase in the absorbance of microwave energy and generation of heat energy.

In one embodiment of the invention the material of the stationary phase participates in the chemical reaction. In these instances, the stationary phase may include a catalyst, a scavenger, etc. relevant for the desired reaction. The "functionality" of the stationary phase will of course be depending on the characteristics of that material or material constituting the particular stationary phase. For example, silica gel may be responsible for the degradation of excess reagents (example 3 (ii)) or scavenging of HCl. In some cases the stationary phase may even be modified in order to obtain certain characteristics in relation to the separation process, e.g. by using a reverse-phase particulate material.

When the chemical reagents are introduced onto the bulk of the stationary phase in solution, the solvent or solvent mixture should be chosen in order to optimise the solubility of the chemical reagent in the solvent as well as the reaction rate of the following chemical reaction. The reagents are suitably added separately so that the reaction does not occur before the reagents are added to the controlled environment of the stationary phase. This being said, it is possible combine two or more of the reagents on beforehand, but it is important with respect to the overall method (in particular with regard to reproducibility) that the reaction proceeds in the stationary phase. Furthermore, it is possible to add more of one or more of the reagents after the reaction has proceeded for a while, just as it is envisaged that it will be relevant to add quenching reagents before performance of the separation step. The latter is however normally not necessary as the reagents normally will be separated from the compounds in the separation step.

In a preferred embodiment of the invention different chemical reactions are performed in parallel in the same bulk of stationary phase providing a library of compounds. The different chemical reagents involved in the synthesis of the desired compounds are introduced to well-defined areas of the bulk of stationary phase providing the reaction mixtures, which will give, rise to the desired compounds. It should be noted that a library of compounds may either be prepared by addition of different chemical reagents to the same area of the bulk with the intention to provide a reaction mixture which purposely gives rise to more than one compound, or by addition of chemical reagents to different areas of the bulk with the intention to provide several reaction mixtures which gives rise to preferably only one compound. It should be understood that the above possibilities may be combined so as to provide several compounds within each of a plurality of discrete areas of a bulk of a stationary phase.

This being said, it is obvious that the synthesis can be considered as performed in "one-dimension" (defined as the X-axis—see FIG. 3) of a three-dimensional bulk as substantially no migration of the reaction mixture occurs during the synthesis step.

Separation of the compounds is performed by allowing at least one of the compounds of the reaction mixture, e.g. reaction product(s), side products or unused chemical reagents, to migrate in the bulk of the stationary phase.

The migration may be passive, but will most often be forced by application of e.g. chromatographic means (eluents) or by application of an electric field (electrophoresis).

The applied chromatographic means depends on the character of the stationary phase and the shape of the backing. The separation of the compound(s) may be performed in the presence of a liquid phase, such as in thin-layer chromatography, paper chromatography and column chromatography.

The liquid phase comprises a solvent or mixture of solvents and optionally one or more auxiliary agents. Examples of liquid phases are mixtures of ethyl acetate/hexane, methanol/dichloromethane/ammonia, methanol/acetonitrile/ammonium phosphate and n-butanol/pyridine/water/glacial acetic acid.

Alternatively, the separation may be conducted in the presence of an electric field, such as in gel electrophoresis or a combination thereof. Separation of the compound(s) may be performed one or more times, in one or more directions. A chemical reaction or parallel synthesised chemical reactions may be separated in two directions by allowing migration of the compounds in the bulk of stationary phase in one direction, drying the bulk of stationary phase and subsequently rotating the bulk of stationary phase 90 degrees before the second separation. Separation in different directions may be done according to different properties of the compounds, e.g. separation is done according to the charge of the compounds in one direction and according to the size of the compounds in another direction.

Figure 3:
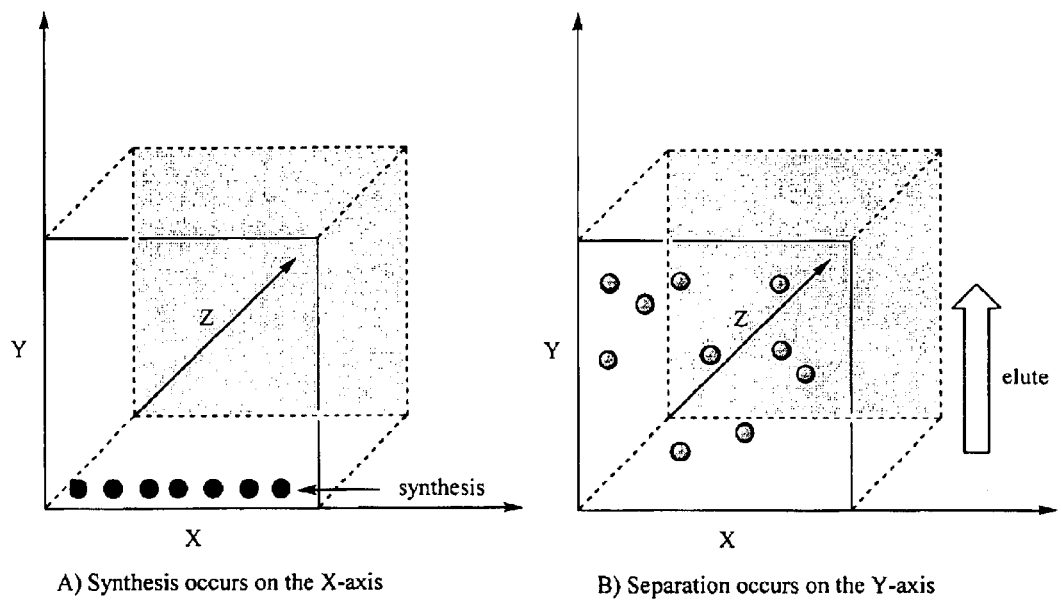
FIG. 3 illustrates a three dimensional representation of one embodiment of the method according to the invention: the synthesis of the compounds are performed along the X-axis (A), separation of the synthesised compounds takes place along the Y-axis (B), and screening of the separated compounds takes place along the Z-axis via transferral or diffusion of the compounds into or onto another medium (C).
Figure 3:
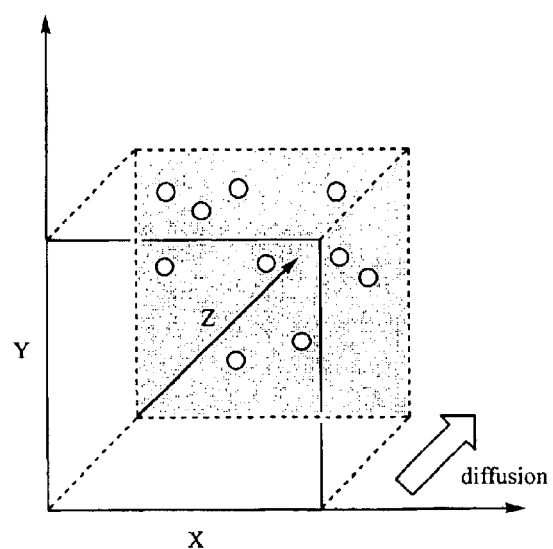

Following the above, it appears that the separation of the compounds normally will take place in a direction nonparallel to the X-axis (defines as the Y-axis—see FIG. 3)

Undesired areas or regions may be transferred or grafted onto another medium, e.g. filter paper while the stationary phase is still saturated with solvents by pressing the other medium on top of the stationary phase.

Figure 4:
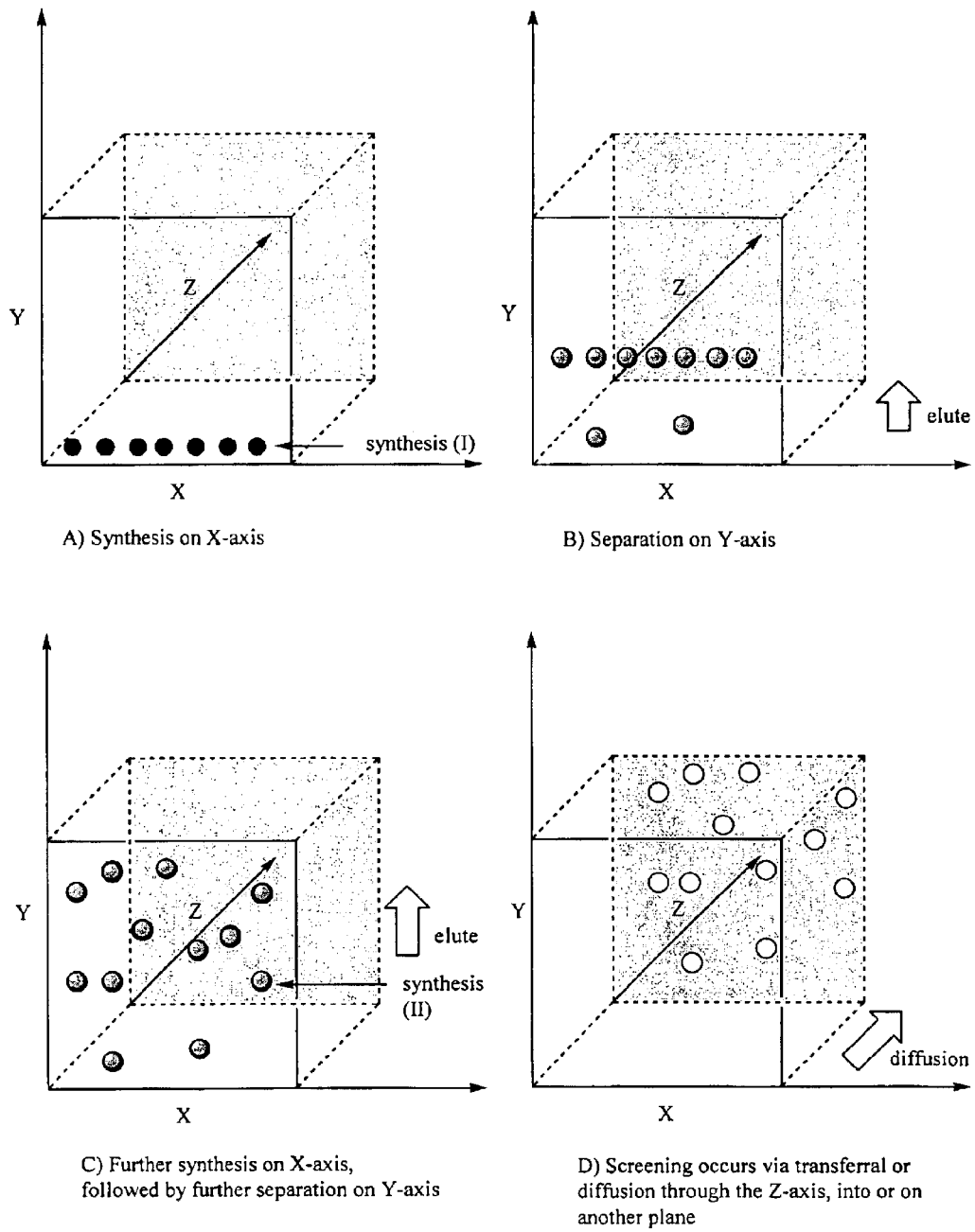
FIG. 4 illustrates a three dimensional representation of one embodiment of the invention, wherein multiple synthesis and separation steps are performed in the X- and Y-axes (A)(B)(C), followed by screening via transferral or diffusion through the Z-axis, into or onto another medium (D).
Figure 5:
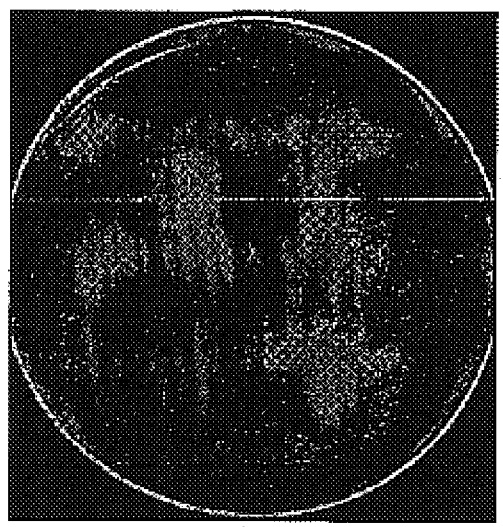
FIG. 5 shows the screening of separated compounds (sulfonamide reference substances) on a TLC plate against Gram negative organisms (*Serralia maracescens*) and Gram positive organisms (*Bacillus subtilis*), respectively. The active zones are seen as white or off-white areas compared with the unaffected areas.
Figure 5:
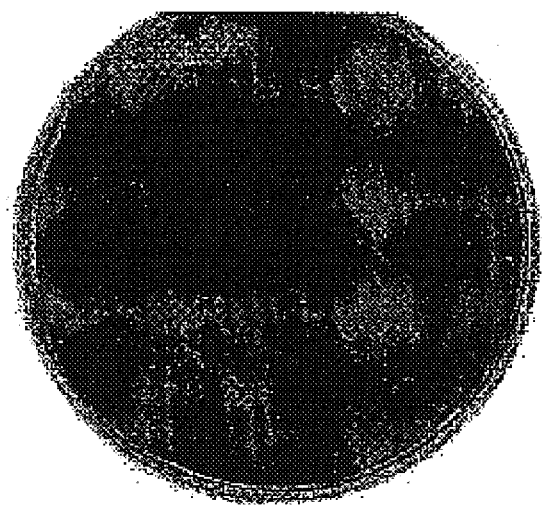
Figure 6:
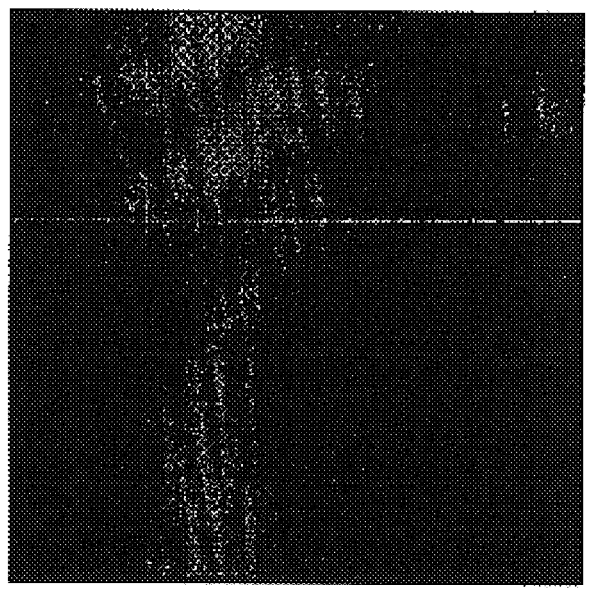
FIG. 6 shows a concentration gradient on a TLC plate of 4 active components to determine minimum growth inhibition of *Serratia marcescens*. The plate was visualised by UV light prior to the assay (A) and is shown after assay (B).
Figure 6:
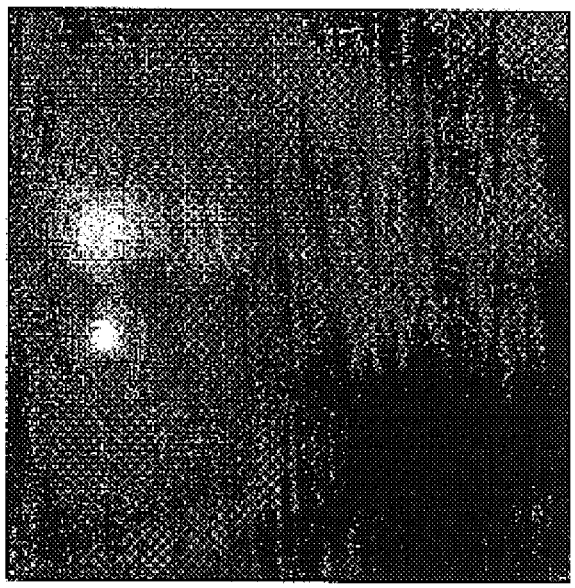

As Illustrated in FIG. 4, the synthesis and separation steps may be followed by a further synthesis and/or separation step before screening. As mentioned above, a further separation step may be performed in a direction which is substantially parallel or non-parallel relative to the direction of the first separation.

Screening of the separated compounds comprised in the bulk of the stationary phase may be performed using biological, chemical or biochemical methods like: bioautographic techniques, overlay techniques, immunostaining, autoradiographic techniques, enzymatic analysis, derivatisation, receptor-binding assays, reporter gene assays, cell proliferation assays, physiologic assays, transient transfection and melanophor pigment-translocation assays. Analytical methods such as detection of catalytic activity by changes in absorption of light or by detection of fluorescence due to a cleaved substrate can also be used. In a preferred embodiment, however, the screening step involves an assay for determining the biological effect of the compounds. This being said, it is preferred that the screening involves either a microorganism or an enzyme, preferably a microorganism.

Screening on the plate can be performed in the traditional manner, e.g. as with bioautographic techniques, autoradiographic screening, immunoassay or enzyme inhibition techniques. The plate can be sprayed with specific fluorescent probes to detect active structures or interactions. The separated compounds are be transferred or blotted from the plate's matrix onto a membrane or filter paper as the initial phase of the screening step (FIG. 3). Typical membranes used in blotting include, but are not restricted to, polyvinylidene difluoride or nitrocellulose and screening can be performed as normal with the added advantage of facilitating diffusion and washing processes during screening. Screening is not restricted to blotting techniques and other hybrid procedures may also be used, e.g. ELISAGRAM where TLC is used in tandem with immunoblotting and competitive ELISA.

Zones of activity or inactivity can be detected and this information used for further study. The screening may involve looking for an optimal property in the library either by analytical methods or by physical methods that may require further interaction of the compounds in the library. Other forms of screening may be performed, but are not limited to those as described in "Combinatorial Chemistry: Synthesis and Application" eds. S. R. Wilson and A. W. Czamik, John Wiley &Sons Inc., NY, 1997, "High Throughput Screening" ed. J. P. Devlin, Marcel Dekker Inc., NY, 1997, "Analytical Methods in Combinatorial Chemistry" B. Yang. Technomic Inc., 2000, "Combinatorial Peptide Library Protocols" ed. S. Cabilly, Humana Press, Totowa, N.J., 1998, and C. P. Woodbury Jr, et al, J. Chromatogr. B, (1999) 725, 113–137.

It should be noted that the screening of the compounds is initiated while the compounds are still in the stationary phase. Depending on the actual screening method utilised, it is possible that the compound(s) or at least a suitable amount of the compound(s) will migrate so as to reach the proximity of the entities (bacteria, enzymes, etc.) with which the compounds are intended to interact. It will therefore be understood that the compounds may actually reach the surface of the bulk of the stationary phase or even migrate into a medium adjacent to the stationary phase. This phenomenon is indicated in FIGS. 3 and 4 where the compounds are expected to migrate parallel with the "Z-axis".

This being said, it is also possible to divide the bulk of the stationary phase into smaller portions, e.g, dividing the bulk with or without backing by cutting or by scraping a part of the stationary phase off the backing, and use such portions for the screening step. It is however desirable that the bulk of the stationary phase remains essentially intact throughout the method.

The separated compounds may be analysed in an optional step either in the bulk of stationary phase or as isolated samples. Different methods for analysis include but are not restricted to irradiation with ultra violet-fight, densitometry with for example ultra-violet or infra-red detection, Raman spectroscopy, electrochemical detection, mass spectrometry, e.g. MALDI (Matrix Assisted Laser Desorption Ionisation), SALDI (Surface Assisted Laser Desorption Ionisation), and chromogenic methods where the separated compounds are stained usually by derivatisation as described in "Thin-Layer Chromatography" by B. Fried and J. Sherma ($4^{th}$ ed., Chromatographic Science Series Volume 81, Marcel Dekker, Inc., New York, 1999, Viii+499 pp.). The use of ultra-violet light requires that the synthesised compound(s) comprises a chromophore. Densitometry is advantageous as it can be used for quantification purposes. MALDI and SALDI may also be used on the surface of the bulk of stationary phase for characterisation purposes. The analysis also allows for quantification if necessary, e.g. by use of a densitometer or FID (Flame Ionisation Detector). Quantification is largely problematic in combinatorial and parallel synthesis. Signal producing systems such as radio labelling, enzyme labelling or fluorophore labelling can however also be used. The optional analysis step may be performed either between the synthesis step and the separation step or between the separation step and the screening step. Also the analysis of the compounds (e.g. by destructive methods) may be performed on compounds of a duplicate stationary phase.

The invention may be used in vast number of technical fields where modification (synthesis—e.g. derivatisation) of target molecules is followed by separation and final screening of the target molecule derivative.

Thus, as reagents (substrates) for the chemical reactions involved in the method of the invention may be used: metabolites of natural compounds, fermentation products, and unknown compounds from different sources, catalysts and agrochemicals such as pesticides and herbicides. Further substrates to be used are dioxins, polycyclic aromatic hydrocarbons and polychlorinated biphenyls, explosives and their degradation products, drugs, e.g. narcotics, analgesics, CNS stimulants, and tranquillisers.

In one embodiment of the invention the method is used in the synthesis and screening of combinatorial libraries such as libraries of arylpiperazines, sulfonamides, amino acids, amides, alcohols and amino alcohols, aldehydes, amino aldehydes as well as libraries of compounds derived from multi-component reactions.

In a particular embodiment of the invention the method is used in the discovery and optimisation of lead compounds for drug development.

In a further embodiment of the reaction the method is used in the optimisation of reaction conditions such as in microwave assisted reactions.

In yet another embodiment of the invention the disclosed method is used in the analysis of organic or inorganic anions together with metal cations such as $Ni^{2+}$, $Cu^{2+}$, $Co^{2+}$, $Fe^{2+}$, $Fe^{3+}$, toxic anions such as arsenate, arsenite, azide and cyanide, organic or inorganic cations such as alkylamines, alkali metal ions and alkaline-earth metal ions, common inorganic anions such as chloride, bromide, iodide, fluoride, sulfite and phosphate, and in the analysis of water pollutants, dioxins, polycyclic aromatic hydrocarbons, polychlorinated biphenyls, explosives and their degradation products, organic acids, biomolecules such as proteins, peptides, DNA, RNA, oligodeoxynucleotides and oligoribonucleotides, radical scavengers and oxidants/antioxidants. Furthermore, the method can be used in the development of chiral analytes and support materials for use in the synthesis and separation of drugs such as narcotics, analgesics, CNS stimulants, tranquillisers.

The present invention discloses a less time consuming and more cost efficient method for synthesis and screening of chemical compounds. The primary advantage of the present invention lies in that screening is performed on the same medium as in which the chemical reaction(s) was performed and that preceding work-up of the reaction mixture(s) is not required. A further advantages of the present invention is that there is no need for optimisation of the involved chemical reaction(s) and that vital information may be gained by simultaneously testing of byproducts and unused chemical reagents.

The invention is further disclosed in the following examples. The examples are riot meant to limit the invention but serve only as illustration of the invention.

EXAMPLES

Example 1

Synthesis

5 µl, 0.06 mmol pyrrolidine was applied as a single spot to a plastic backed TLC plate (20×50 mm, 0.25 mm thick, Silica gel 60F254). 5 µl, 0.04 mmol benzyl bromide was then applied to the same area. In another experiment the reactants were applied to the plate in solution, e.g. as 0.1 M solutions in dichloramethane, and the solvent allowed to evaporate from the plate. The scheme below shows the reaction between pyrrolidine and benzyl bromide.

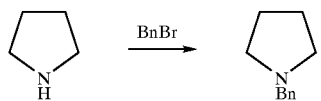

Separation

The TLC plate was eluted with 10% $MeOH-CH_2Cl_2$. The solvent was then allowed to evaporate from the plate. Spots were visualised in a nondestructive manner with ultra-violet light of wavelength 254 nm. Spots could also be visualised in a destructive fashion by derivatisation if necessary, e.g. by use of a ninhydrin staining reagent on a duplicate plate, and the product areas cross-correlated.

Optional analysis

Product spots could be analysed directly on the plate by mass spectrometry. Alternatively, the spots from a duplicate plate were analysed by first scraping the desired areas from the plate and by dissolving the substrates in a suitable solvent and filtering off the product. Routine analysis could then be performed by, e.g. NMR, GCMS, etc.

Screening

Screening was performed in accordance with a standard method for screening for antimicrobial activity: Bacteria were grown on standard NA plates (Difco Bacto Nutrient Broth agarose) pH 7 before use. Sea Plaque Agarose (low gelling temperature agarose, 20 g, FMC Bio Products) and 8 g of a carbon source, BUGM (Biolog Universal Growth Medium) were mixed in 1 L distilled water and irradiated for 10 min in a domestic microwave oven. The medium was allowed to cool and was stored at 35° C. in a water bath. To this medium was added 2 mL concentrated bacteria suspension (ca $1-10×10^3$ cells per mL) giving a final concentration of approximately $1-10×10^5$ cells per mL Approximately 30 mL of this medium was used and poured over a TLC plate (10×10 cm) in a Petri dish and the plates incubated at 30° C. Standards (10 µL of a 1 mg/mL solution in methanol) were applied to the TLC plate. Typical reference standards used included Sulfaguanidine, Sulfapyridine, Sulfathiazole, Sulfadiazine, Sulfamethoxazole and Amphotericin.

An agar gel containing the bacterium *Serracia marcescens* was poured over the TLC plate at 40° C. The red coloured gel was allowed to cool and the plate left overnight at room temperature. The following day white inhibition zones were clearly visible around the product, indicating that the product had antibacterial activity against this strain. Unreacted benzyl bromide also showed some activity against this strain.

Example 2

Synthesis in Parallel

Figure 11:
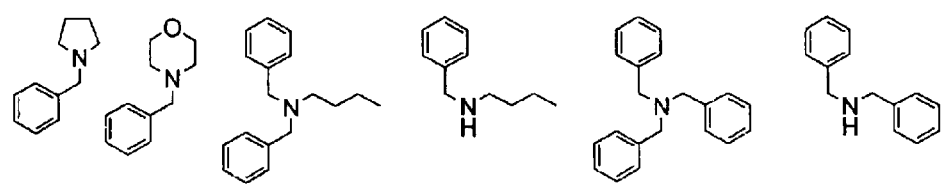
FIG. 11 shows a library of synthesised secondary and tertiary amines.

A library of secondary and tertiary amines (FIG. 11) was synthesised in a parallel using the corresponding starting materials and the methodology described in Example 1. These were synthesised from primary and secondary amines (10 µl) by their reaction with 5 µl benzyl bromide on an aluminium backed TLC plate (50×50 mm, 0.25 mm thick, Silica gel 60F254). The primary amines afforded a mixture of both secondary and tertiary amine products that could be screened simultaneously in the same assay. After synthesis the products were separated by elution as in Example 1B.

Analysis and screening were similarly performed as before. The reaction schemes are shown below.

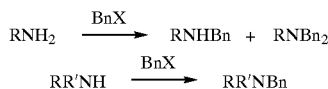

Example 3

(i) Microwave Assisted Parallel Synthesis

Figure 12:
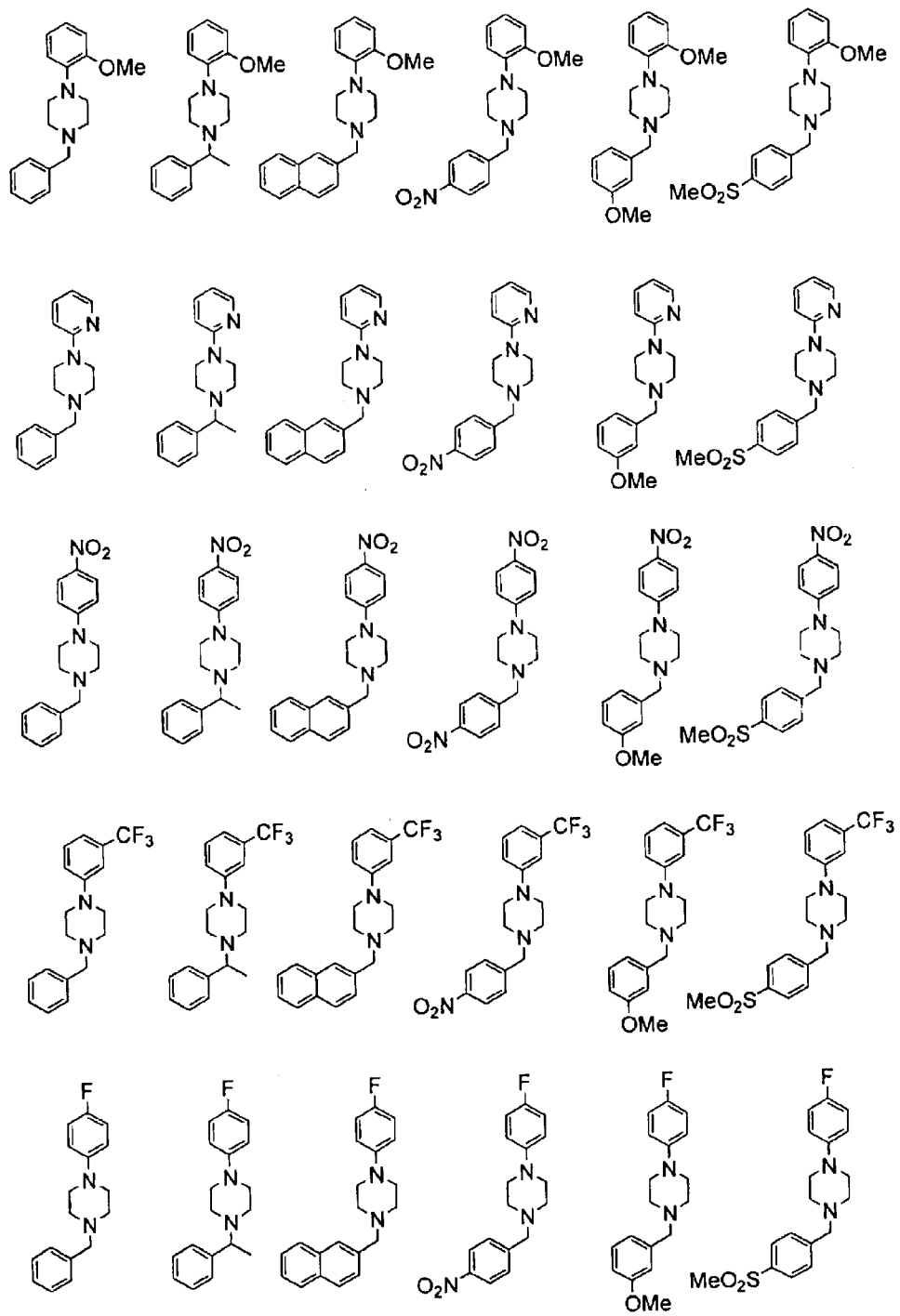
FIG. 12 shows a library of synthesised of 1-arylpiperazines.

A library of piperazines (FIG. 12) was synthesised in a parallel and similar fashion to that in Example 1. These were synthesised from 1-arylpiperazines. 100 µl of a 1 mmol solution of 1-arylpiperazines in $CH_2Cl_2$ or DMSO were reacted with 50 1 µl of a 1 mmol solution of benzyl halide derivatives in $CH_2Cl_2$ or DMSO. Reactions were optimised in this case by use of microwave radiation. After application of reagents onto a glass-backed TLC plate (100×100 mm, 2 mm thick, silica gel 60F254), the plate was placed in a domestic microwave oven (Electrolux NF4884). The plate was irradiated at about 585 W for 5 min to facilitate reaction. A beaker of 50 mL water was placed near the plate to act as a heat sink. The water absorbs a portion of the microwave energy and is used to fine tune the energy absorbed by the reactions. After cooling of the plate, the products were separated and screened as in Example 1 yielding products that showed growth inhibition of *Serracia* sp. The scheme below illustrates the reaction outlined in Example 3.

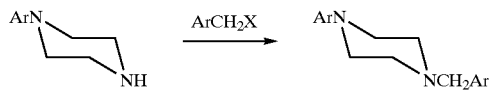

(ii) Microwave Assisted Parallel Synthesis

Figure 13:
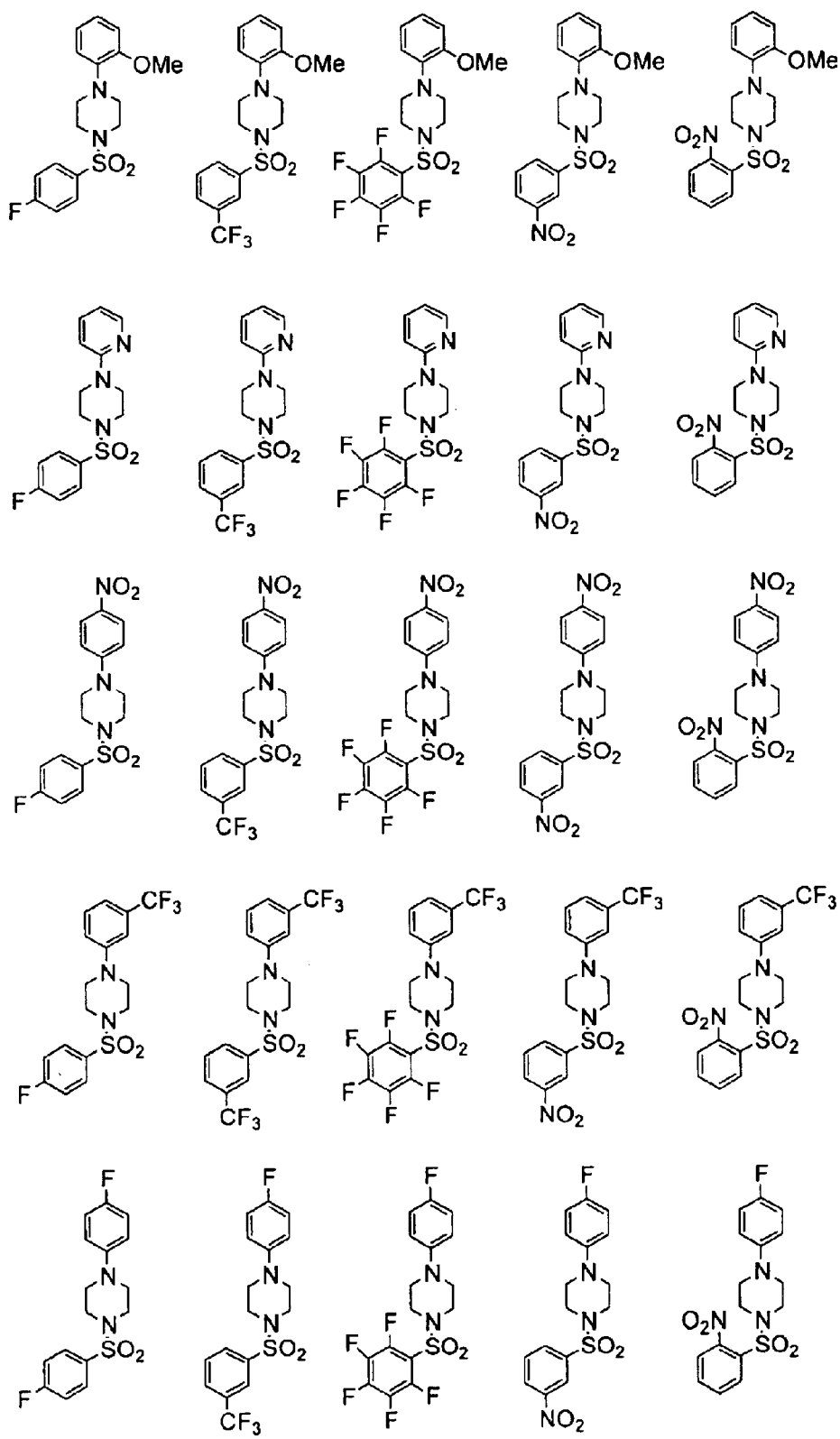
FIG. 13 shows a library of synthesised of sulfonamides.

A library of sulfonamides (FIG. 13) was synthesised in a parallel and similar fashion to that in Example 3i. These were synthesised from 1-arylpiperzines.

Figure 7:
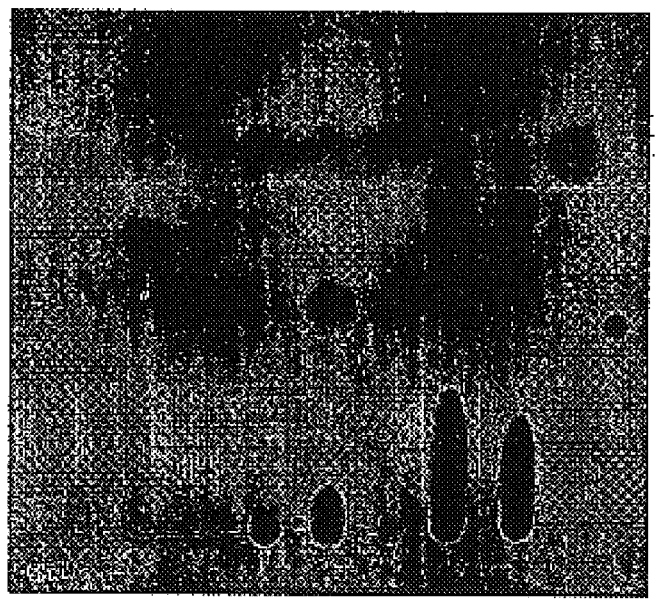
FIG. 7 shows a number of sulfonamides after synthesis and separation on TLC, and comparison of their synthesis both with (A) and without microwave radiation (B).
Figure 7:
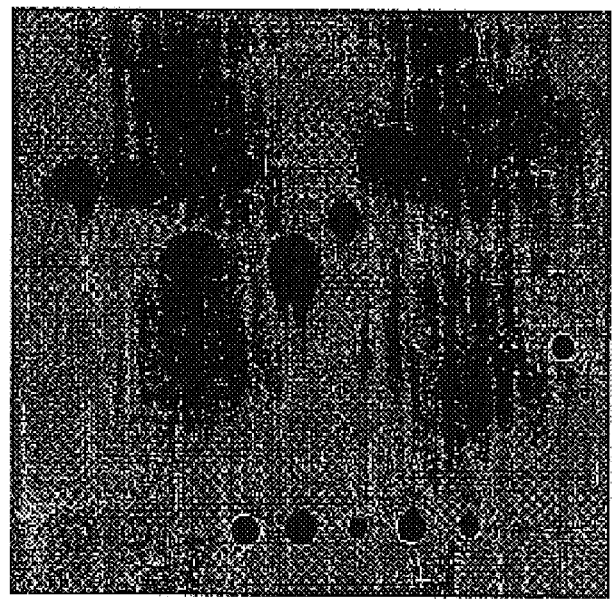
Figure 8:
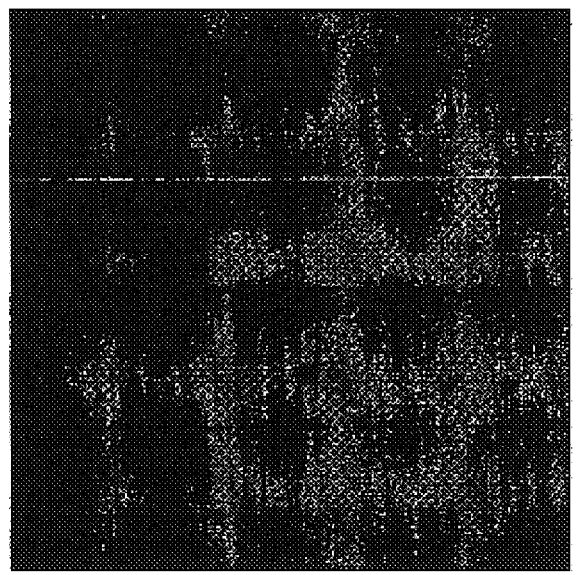
FIG. 8 shows a library of synthesised piperazines after separation on TLC (A), and subsequent biological screening on the TLC plate (B). The separation was effected by elution from the top and bottom into the middle of the plate.
Figure 8:
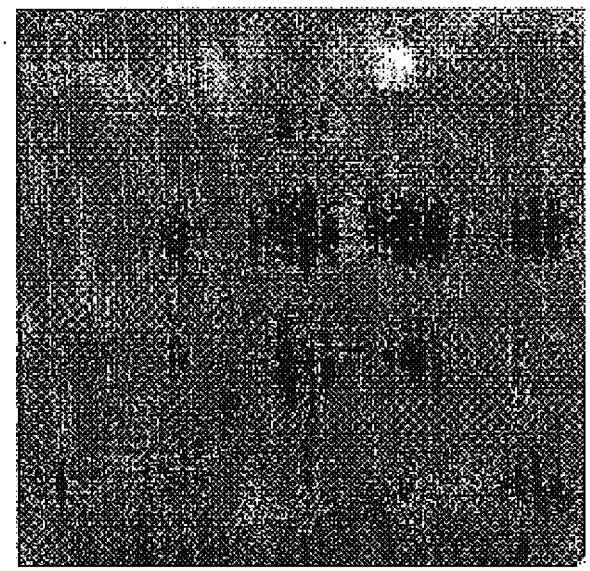

4 µl of a 1 mmol solution of 1-arylpiperazines in $CH_2Cl_2$ were reacted with 8 µl of a 1 mmol solution of aryl sulfonylhalide derivative in $CH_2C6$. Reactions were optimised in this case by use of microwave radiation (FIG. 7). After application of reagents onto a glass-backed TLC plate (200×200 mm, 0.25 mm thick, Silica gel 60F254), the plate was placed in a domestic microwave oven (Electrolux NF4884). The plate was irradiated at about 585 W for 5 min. A beaker of 50 mL water was placed near the plate to act as a heat sink. The water absorbs a portion of the microwave energy and is used to fine tune the energy absorbed by the reactions. After cooling of the plate, the products were separated and screened as in Example 1 (FIG. 8). Excess sulfonylhalide was advantageously degraded to the corresponding sulfonic acid making analysis and screening easier. Several products showed activity against *Serracia* sp. The following scheme is representative of this type of reaction.

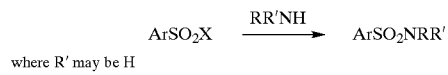

where R' may be H

Example 4

Parallel Synthesis

Figure 14:
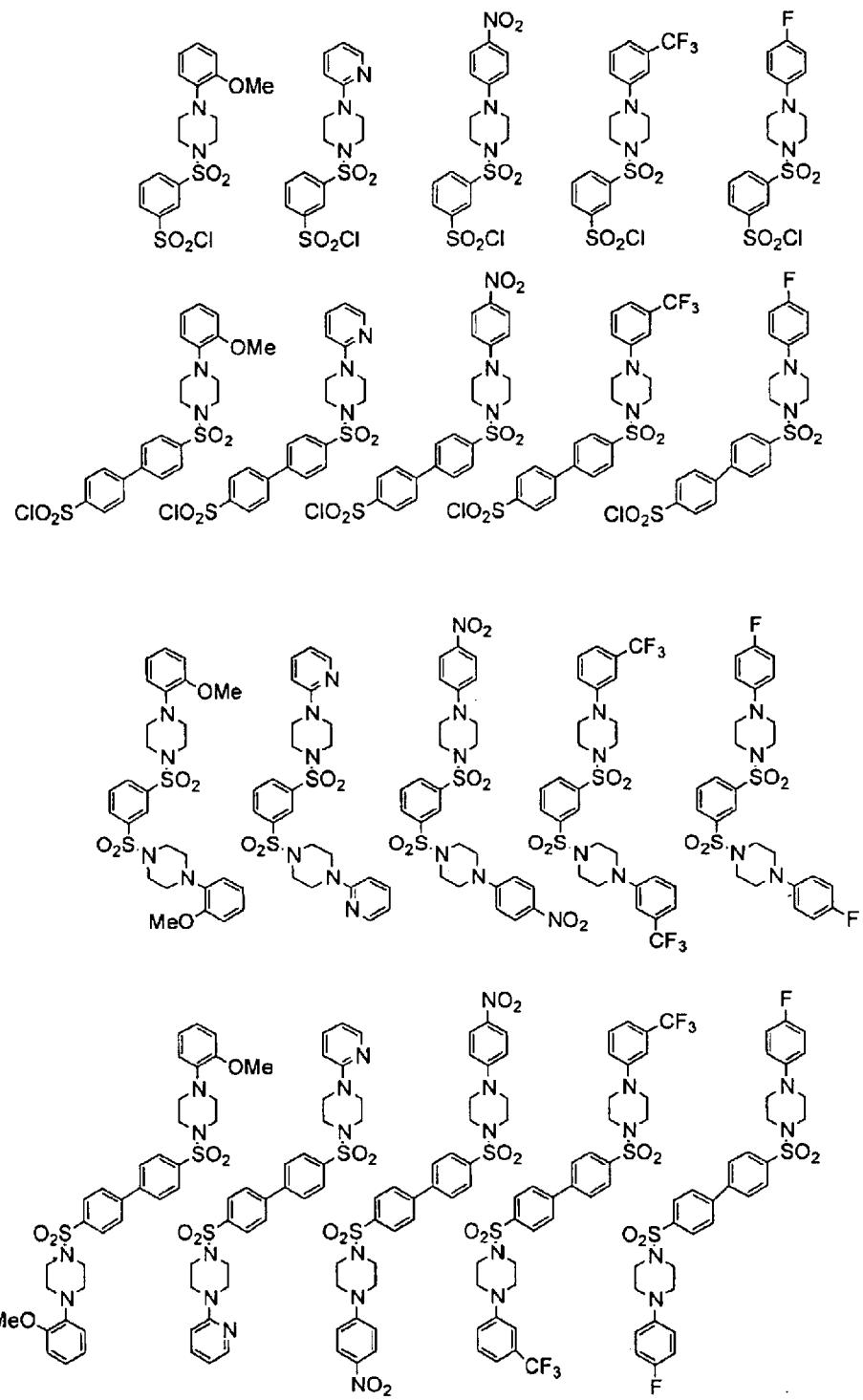
FIG. 14 shows a mixed library of synthesised mono- and bissulfonamides.

A library of mono and bissulfonamides (FIG. 14) was synthesised in a parallel and similar fashion to that in Example 2. These were synthesised from 1-arylpiperazines. 5 µl of a 1 mmol solution of 1-arylpiperazines in $CH_2Cl_2$ were reacted with 10 µl of a 1 mmol solution of bissulfonylhalide derivatives in $CH_2Cl_2$ on a glass-backed TLC plate (50×100 mm, 0.25 mm thick, silica gel 60F254). The products were separated and screened as in Example 1. Several products showed growth inhibition of *Serracia* sp. The following scheme shows the synthesis of both mono and bissulfonamides.

Example 5

Deprotection

Figure 15:
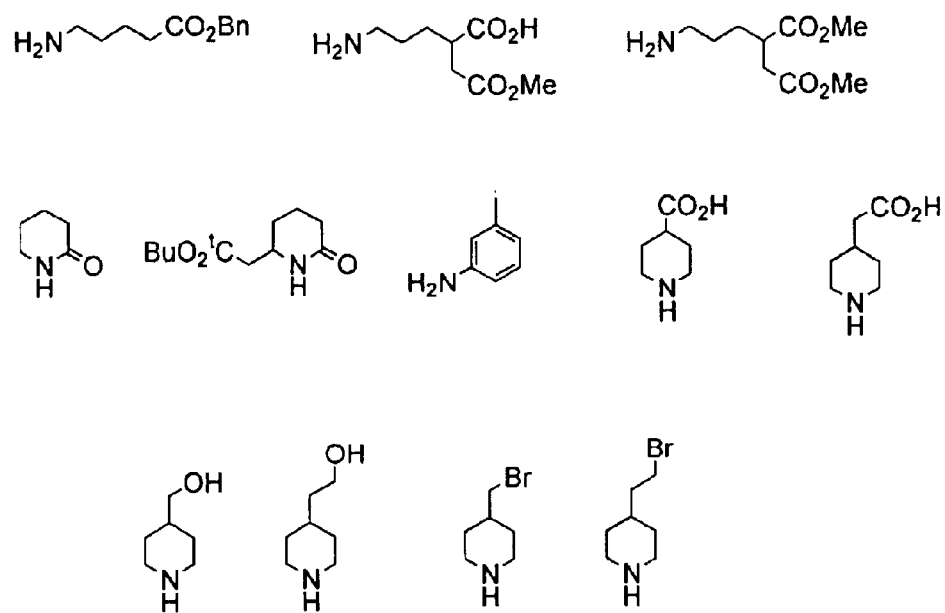
FIG. 15 shows a mixed library of synthesised amines, amides and amino acids.
Figure 16:
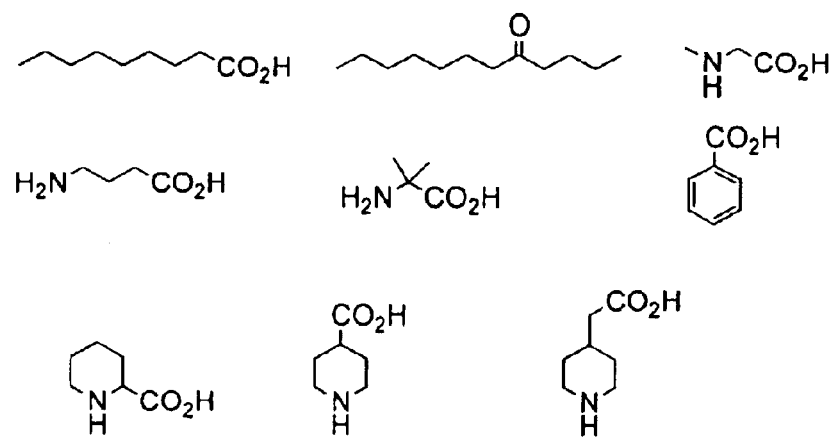
FIG. 16 shows a mixed library of synthesised ketones, carboxylic and amino acids.

A library of N-Boc protected amines, amides and amino acids (10 mg) was deprotected in the following manner. After synthesis the substrates on a glass-backed TLC plate (50×100 mm, 0.25 mm thick, silica gel 60F254) were subjected to microwave radiation at 585 W for 10 min in a domestic microwave oven (Electrolux NF4884) to facilitate deprotection. A beaker of water (50 mL) was placed near the plate to act as a heat sink. The water absorbs a portion of the microwave energy and is used to fine tune the energy absorbed by the reactions. The deprotected compounds (FIG. 15) were then separated on the plate and screened as in Example 1. Typical deprotections are listed below.

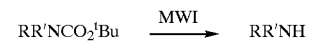

where R' may be H

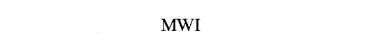

where R may be H

where R' may be H

Example 6

Oxidation

Figure 18:
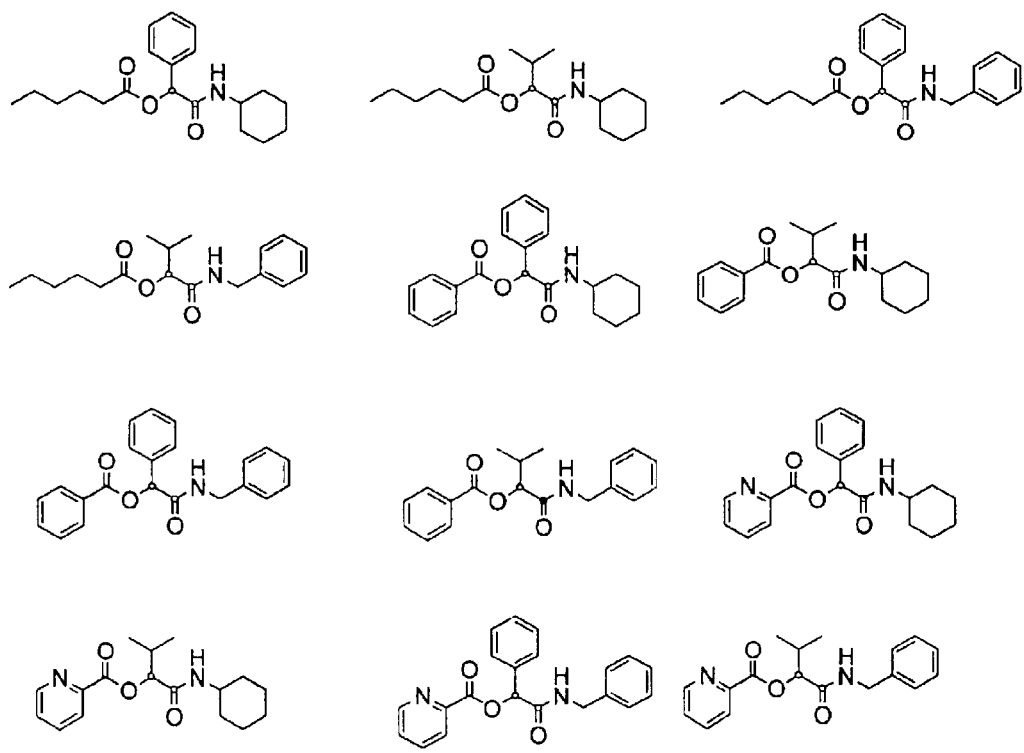
FIG. 18 shows a library of α-(acyloxy)carboxamides synthesised via a Passerini reaction.

A library of alcohols, aldehydes, amino alcohols and amino aldehydes (5 µl of a 1 mmol solution in $CH_2Cl_2$) were oxidised with Jones reagent ($CrO_3/H_2SO_4$, 10 µl of a 1 mmol solution in acetone). The substrates were applied to a glass-backed TLC plate (50×100 mm, 0.25 mm thick, silica gel 60F254) and excess Jones reagent applied. The TLC plate was then irradiated at 585 W for 10 min in a domestic microwave oven (Electrolux NF4884) to assist oxidation. A beaker of water (50 mL) was placed near the plate to act as a heat sink. The water absorbs a portion of the microwave energy and is used to fine tune the energy absorbed by the reactions. The resultant ketones, carboxylic and amino acids (FIG. 18) were then separated on the plate and screened as in Example 1. Typical oxidations are listed below.

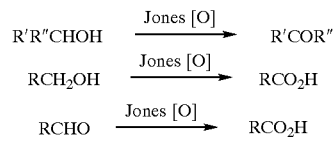

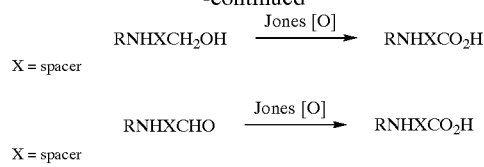

Example 7

Oxidation and Simultaneous Deprotection

Figure 17:
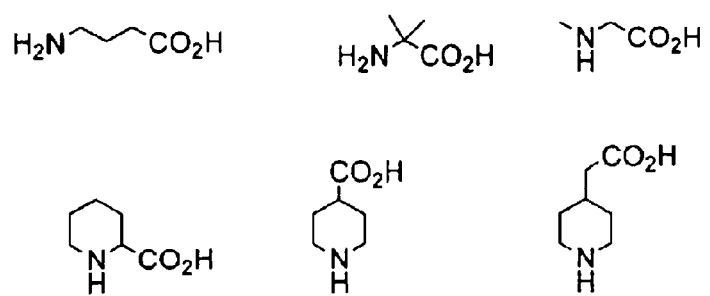
FIG. 17 shows a library of synthesised amino acids.

A library of N-Boc protected amino alcohols and amino aldehydes (5 µl of a 1 mmol solution in $CH_2Cl_2$) were simultaneously deprotected and oxidised with Jones reagent ($CrO_3/H_2SO_4$, 10 µl of a 1 mmol solution in acetone). The substrates were applied to a glass-backed TLC plate (50×100 mm, 0.25 mm thick, silica gel 60F254) and excess Jones reagent applied. The TLC plate was then irradiated at 585 W for 10 min in a domestic microwave oven (Electrolux NF4884) to facilitate both oxidation and deprotection. A beaker of water (50 mL) was placed near the plate to act as a heat sink. The water absorbs a portion of the microwave energy and is used to fine tune the energy absorbed by the reactions. The resultant deprotected amino acids (FIG. 17) were then separated on the plate and screened as in Example 1. The simultaneous oxidation/deprotection schemes are shown below.

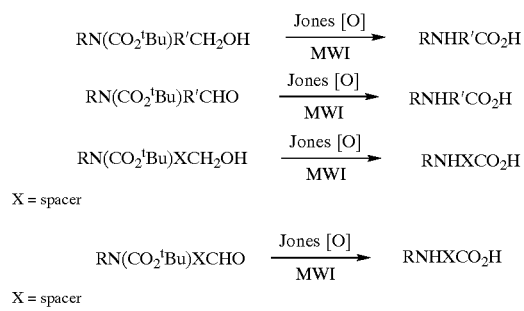

Example 8

(i) Multi-Component Reactions

Figure 9:
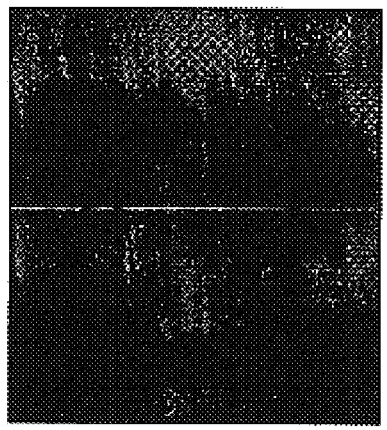
FIG. 9 shows a library of α-(acyloxy)carboxamides (Passerini reaction) after synthesis and separation on TLC (A), and subsequent biological screening of the compounds against Gram negative bacteria (*Serratia marcescens*) (B) and Gram positive bacteria (*Bacillus subtilus*) (C), respectively.
Figure 9:
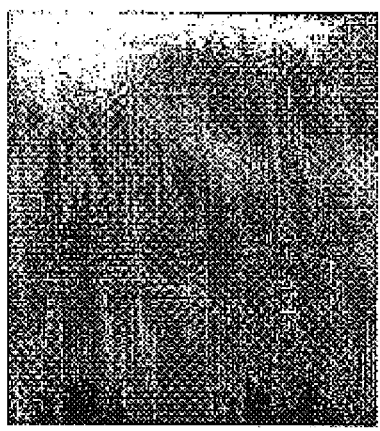
Figure 9:
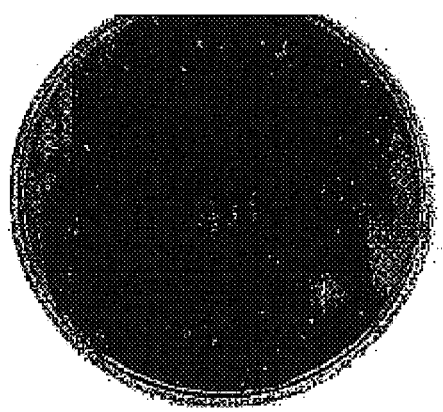

A library (FIG. 18) based on the Passerini reaction was synthesised by reaction of various carboxylic acids (10 µl of a 1 mmol solution in $CH_2C6$) with several aldehydes (10 µl of a 1 mmol solution in $CH_2Cl_2$) and isocyanides (10 µl of a 1 mmol solution in $CH_2Cl_2$) on a glass-backed TLC plate (50×100 mm, 0.25 mm thick, silica gel 60F254) with the assistance of microwave irradiation at 585 W for 5 min in a domestic microwave oven (Electrolux NF4884). A beaker of water (50 mL) was placed near the plate to act as a heat sink. The water absorbs a portion of the microwave energy and is used to fine tune the energy absorbed by the reactions. The products were then separated as in Example 1B and the product spots screened against *Serratia marcescens* as in Example 1. A duplicate plate was screened against *Bacillus subtilis* in a similar screen (FIG. 9). In this case methylene blue was sprayed onto the agar gel after incubation to facilitate identification of inhibition zones. Active areas were seen as white zones on a blue background. The Passerini reaction is illustrated below.

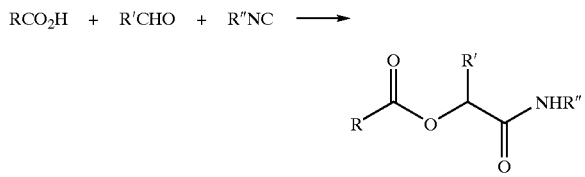

(ii) Multi-Component Reactions

Figure 10:
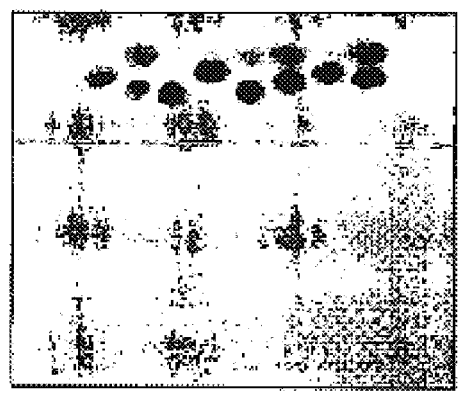
FIG. 10 shows a library of α-aminoacylamides (Ugi reaction) after synthesis and separation on TLC (A), and subsequent biological screening of compounds against Gram negative bacteria (*Serratia marcescens*) (B) and Gram positive bacteria (*Bacillus subtilus*) (C), respectively.
Figure 10:
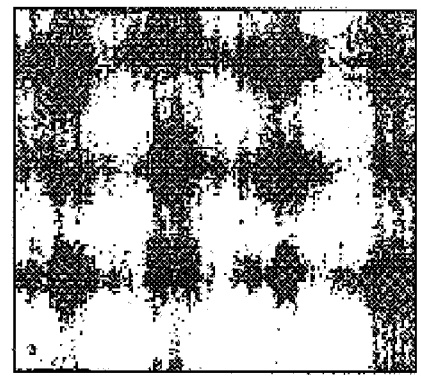
Figure 10:
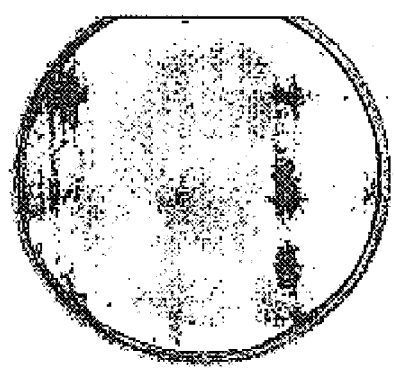
Figure 19:
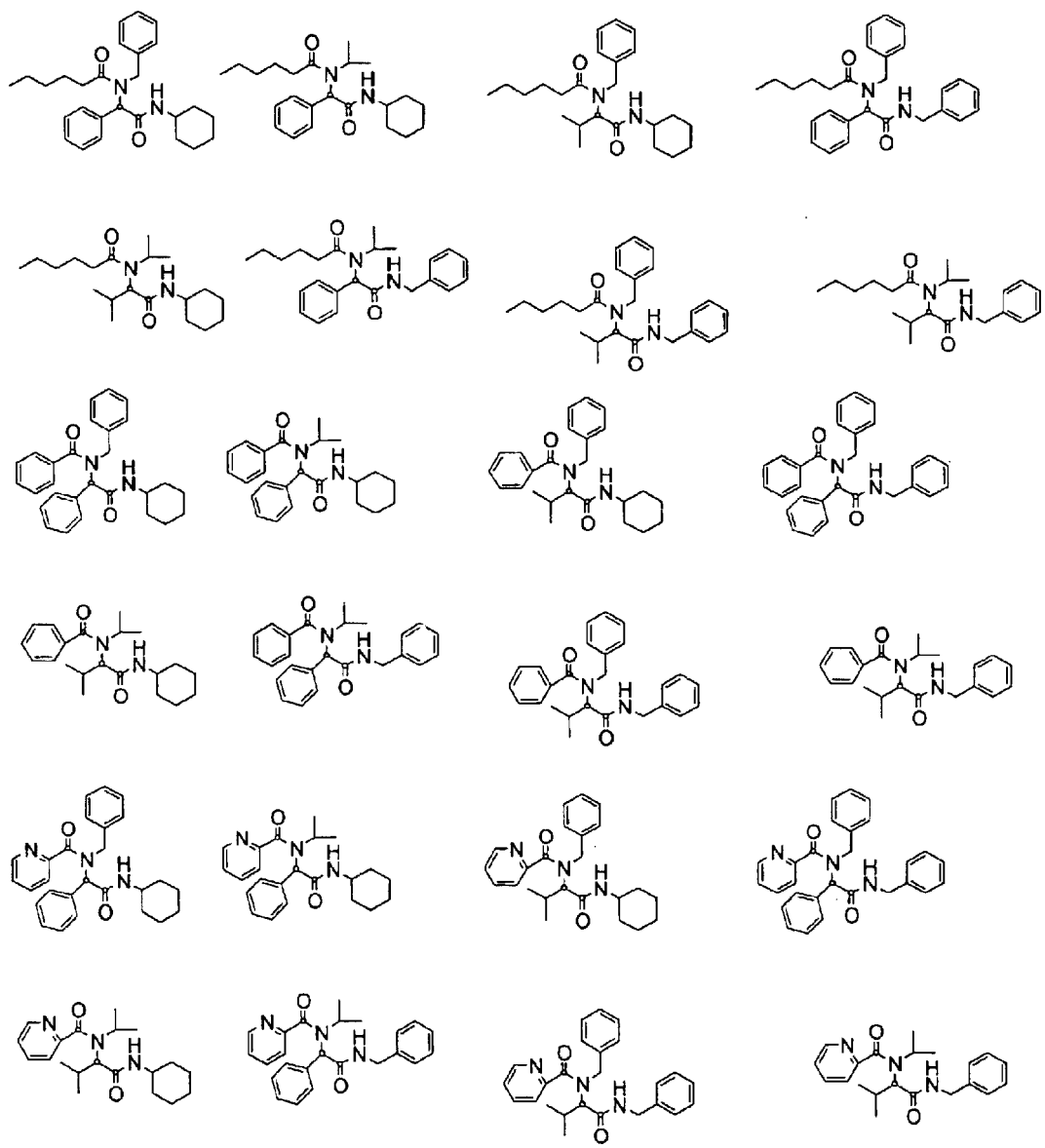
FIG. 19 shows a library of α-aminoacylamides synthesised via an Ugi reaction.

A library (FIG. 19) based on the Ugi reaction was synthesised by reaction of various carboxylic acids (10 µl of a 1 mmol solution in MeOH) with several aldehydes (10 µl of a 1 mmol solution in MeOH), amines (10 pd of a 1 mmol solution in MeOH) and isocyanides (10 µl of a 1 mmol solution in MeOH) on a glass-backed TLC plate (50×100 mm, 0.25 mm thick, silica gel 60F254) with the assistance of microwave irradiation at 585 W for 5 min in a domestic microwave oven (Electrolux NF4884). A beaker of water (50 mL) was placed near the plate to act as a heat sink. The water absorbs a portion of the microwave energy and is used to fine tune the energy absorbed by the reactions. After separation the product spots were screened as in Example 1. A duplicate plate was screened against *Bacillus subtilis* as above (FIG. 10). The Ugi reaction is illustrated below.

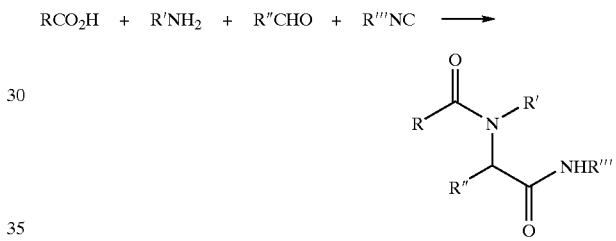

While the invention has been particularly shown and described with reference to preferred embodiments thereof, it will be understood by those skilled in the art that various changes in form and details may be made therein without departing from the spirit and scope of the invention. Accordingly, unless otherwise specified, any dimensions of the apparatus indicated in the drawings or herein are given as an example of possible dimensions and not as a limitation. Similarly, unless otherwise specified, any sequence of steps of the method indicated in the drawings or herein are given as an example of a possible sequence and not as a limitation.

What is claimed is:

1. A method for preparing and screening a plurality of compounds, said method performed in or on a bulk of a stationary phase, the method comprises the sequential steps of
   (a) performing a synthesis of compounds by a chemical reaction performed in the bulk of a stationary phase,
   (b) separating the compounds in or on the same bulk of the stationary phase using a mobile phase; and
   (c) screening of the separated compounds in or on the same bulk of stationary phase,
   wherein said screening involves biological or biochemical methods;
   wherein the stationary phase is a thin-layer chromatography plate and wherein the stationary phase is suitable for sequential synthesis.

2. A method according to claim 1, comprising additional analysis of the separated compounds in the bulk of the stationary phase or an isolated sample of the compounds.

3. A method according to claim 1, wherein the compounds are synthesized in the bulk of the stationary phase by introducing chemical reagents involved in the chemical reaction into the bulk of the stationary phase thereby generating a reaction mixture.

4. A method according to claim 1, wherein each of the chemical reagents is individually introduced into the bulk of the stationary phase.

5. A method according to claim 1, wherein each of the chemical reagents is introduced into the bulk of the stationary phase in a solution.

6. A method according to claim 5, wherein the solution comprises one or more solvents.

7. A method according to claim 1, wherein the reaction mixture is localized in a well-defined area in the bulk of the stationary phase.

8. A method according to claim 1, wherein chemical reagents involved in a specific synthesis of the compounds are introduced to a well-defined area on the bulk of the stationary phase.

9. A method according to claim 1, wherein various syntheses are performed in parallel on separate and well-defined areas of the same bulk of stationary phase.

10. A method according to claim 9, wherein synthesis of the plurality of compounds on the same bulk of a stationary phase provides a library of different compounds.

11. A method according to claim 1, wherein the chemical reaction is assisted by microwave radiation.

12. A method according to claim 11, wherein the chemical reaction is exposed to microwave radiation by placing the bulk of the stationary phase comprising the reaction mixture in a microwave cavity.

13. A method according to claim 1, wherein the stationary phase comprises silica gel, aluminum oxide, cellulose, graphite, molecular sieve and polymers.

14. A method according to claim 13, wherein the stationary phase is silica gel.

15. A method according to claim 13, wherein the stationary phase is aluminum oxide.

16. A method according to claim 13, wherein the stationary phase is polyacrylamide.

17. A method according to claim 1, wherein the bulk of stationary phase is dispersed onto or between an inert backing(s).

18. A method according to claim 17, wherein the inert backing comprises glass, plastic, fibrous materials, paper, metals or mixtures thereof.

19. A method according to claim 17, wherein the layer thickness of the bulk of the stationary phase when dispersed onto or between the inert backing(s) is 10-tm to 5 mm.

20. A method according to claim 17, wherein the combined bulk of stationary phase and inert backing is a silica gel thin-layer chromatography plate with a plastic backing.

21. A method according to claim 17, wherein the combined bulk of stationary phase and inert backing is a silica gel thin-layer chromatography plate with a glass backing.

22. A method according to claim 1, wherein the separation is performed by allowing at least some of the components of the reaction mixture to migrate in the bulk of the stationary phase.

23. A method according to claim 22, wherein the compound(s) are allowed to migrate in the bulk of the stationary phase by application of chromatographic means.

24. A method according to claim 22, wherein the separation of the compounds is performed in the presence of a liquid phase.

25. A method according to claim 24, wherein the liquid phase is a solvent or mixtures of solvents and optionally one or more auxiliary agents.

26. A method according to claim 25, wherein the liquid phase comprises ethyl acetate/hexane, methanol/dichloromethane/ammonia, methanol/acetonitrile/ammonium phosphate and n-butanol/pyridine/water/glacial acetic acid.

27. A method according to claim 1, wherein the biological and biochemical methods are selected from a group consisting of bioautographic techniques, overlay techniques, immunostaining, autoradiographic techniques, enzymatic analysis, derivatisation, receptor-binding assays, reporter gene assays, cell proliferation assays, physiologic assays, transient transfection and melanophor pigment-translocation.

28. A method according to claim 1 for the synthesis, separation and screening of combinatorial libraries of compounds.

29. A method according to claim 28, wherein the compounds of the combinatorial libraries are synthesized by multi-component reactions.

30. A method according to claim 28, wherein the combinatorial libraries comprise compounds such as arylpiperazines, sulfonamides, amino acids, amides, alcohols, amino alcohols, aldehydes and amino aldehydes.

31. A method according to claim 1, wherein the screening step involves the detection of biological effects of a compound interacting with a microorganism or an enzyme.

32. A method according to claim 31, wherein the screening step involves the detection of biological effects of a compound interacting with a microorganism.

33. The method of claim 1, wherein the biochemical methods involve detection of changes in catalytic activity produced by interaction of the compounds and a catalyst by observing changes in absorption of light or detection of fluorescence due to a modification of the compounds or of a substrate.

34. The method of claim 33, wherein said catalyst in an enzyme.

35. A method for preparing a plurality of compounds and screening at least one of said compounds, the method comprises the sequential steps of
   (a) performing a synthesis of compounds by a chemical reaction performed in or on the bulk of a stationary phase,
   (b) separating at least one of the compounds in or on the same bulk of the stationary phase using a mobile phase; and
   (c) screening the at least one separated compound in or on the same bulk of stationary phase, or via transferring or blotting of the at least one said compound from said bulk into or onto another medium;
   wherein said screening involves biological or biochemical methods;
   wherein the stationary phase is a part of a thin-layer chromatography plate or wherein the stationary phase is suitable for performing the method in a three dimensional bulk of the stationary phase.

36. The method of claim 1 or 35, wherein the bulk of the stationary phase is a part of a thin-layer chromatography plate.

* * * * *